(12) United States Patent
Fayyaz et al.

(10) Patent No.: US 10,226,328 B2
(45) Date of Patent: Mar. 12, 2019

(54) SYSTEMS AND METHODS FOR DEPLOYMENT DAMPING IN INTRAOCULAR LENS DEPLOYMENT

(71) Applicant: Novartis AG, Basel (CH)

(72) Inventors: Asif Fayyaz, Euless, TX (US); Jian Liu, Arlington, TX (US); Sudarshan B. Singh, Euless, TX (US)

(73) Assignee: Novartis AG, Lichtstrasse, Basel (CH)

( * ) Notice: Subject to any disclaimer, the term of this patent is extended or adjusted under 35 U.S.C. 154(b) by 230 days.

(21) Appl. No.: 15/239,576

(22) Filed: Aug. 17, 2016

(65) Prior Publication Data
US 2018/0049866 A1 Feb. 22, 2018

(51) Int. Cl.
*A61F 2/16* (2006.01)
*A61F 9/00* (2006.01)

(52) U.S. Cl.
CPC ............ *A61F 2/167* (2013.01); *A61F 2/1672* (2013.01); *A61F 2/1675* (2013.01); *A61F 2/1662* (2013.01); *A61F 2/1667* (2013.01); *A61F 9/0008* (2013.01); *A61F 9/0017* (2013.01); *A61F 2002/1682* (2015.04)

(58) Field of Classification Search
CPC ...... A61F 2/1662; A61F 2/1667; A61F 2/167; A61F 2/1672; A61F 2002/1682; A61F 9/0008; A61F 9/0017
See application file for complete search history.

(56) References Cited

U.S. PATENT DOCUMENTS

| | | | | |
|---|---|---|---|---|
| 2010/0160926 A1* | 6/2010 | Artsyukhovich | ....... | A61F 2/167 606/107 |
| 2014/0171956 A1* | 6/2014 | Helmy | ............... | G01N 21/8422 606/107 |
| 2014/0276901 A1* | 9/2014 | Auld | ..................... | A61F 2/1678 606/107 |
| 2016/0256316 A1* | 9/2016 | Van Noy | ............ | A61F 9/00736 |

* cited by examiner

*Primary Examiner* — Robert Lynch

(57) ABSTRACT

Intraocular lens (IOL) insertion apparatus and methods of use are provided and described herein. An example IOL insertion apparatus may include a handpiece body having a distal tip, a deployment chamber having an opening at a distal end of the handpiece body, and a deployment system disposed within the handpiece body. The deployment system can include a deployment carriage movable between proximal and distal positions within the handpiece body and a deployment plunger with a proximal end secured to the deployment carriage and a distal end to engage a folded IOL. The insertion apparatus may further include a damping feature protruding from a wall of the deployment chamber or a portion of the deployment system. The first damping feature may be positioned and arranged to increase a resistance to movement of the deployment system along a portion of a path traveled thereby between the proximal and distal positions.

16 Claims, 12 Drawing Sheets

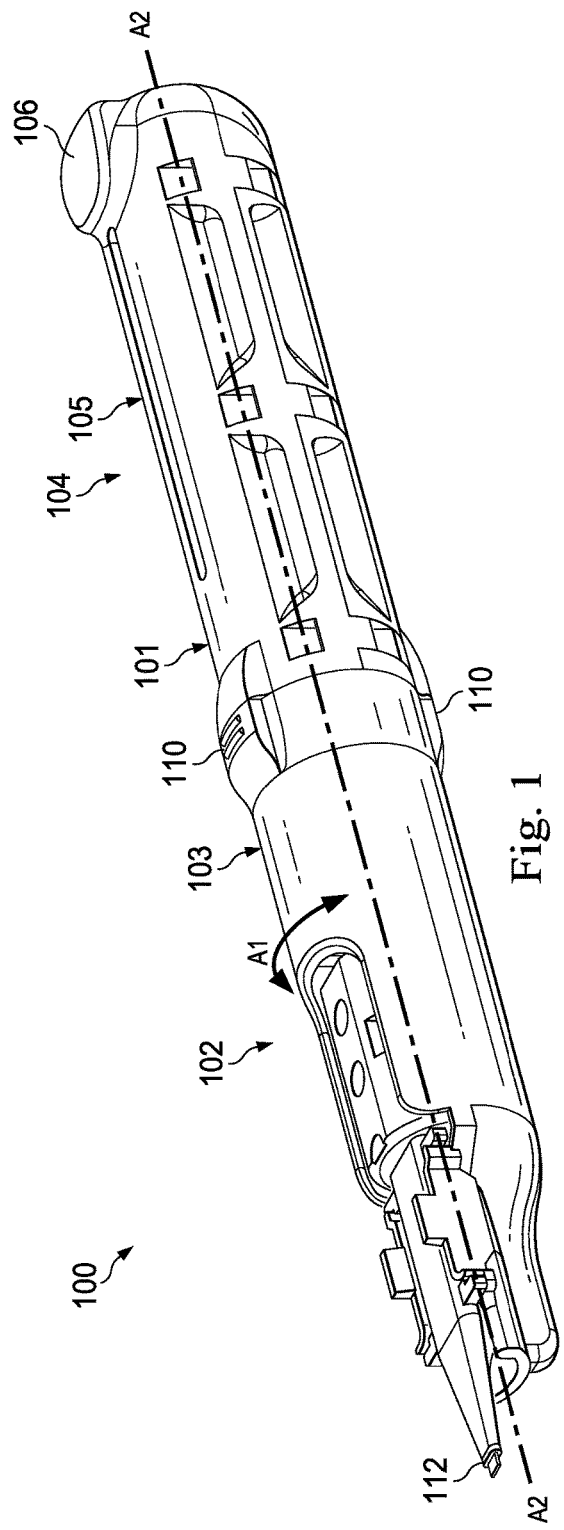
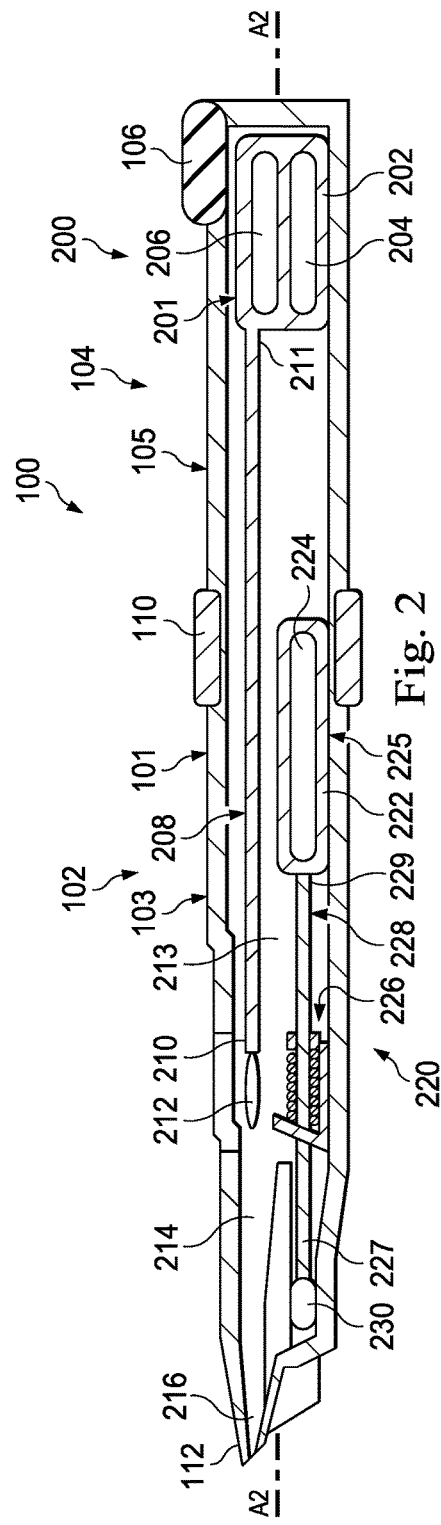
Fig. 1
Fig. 2

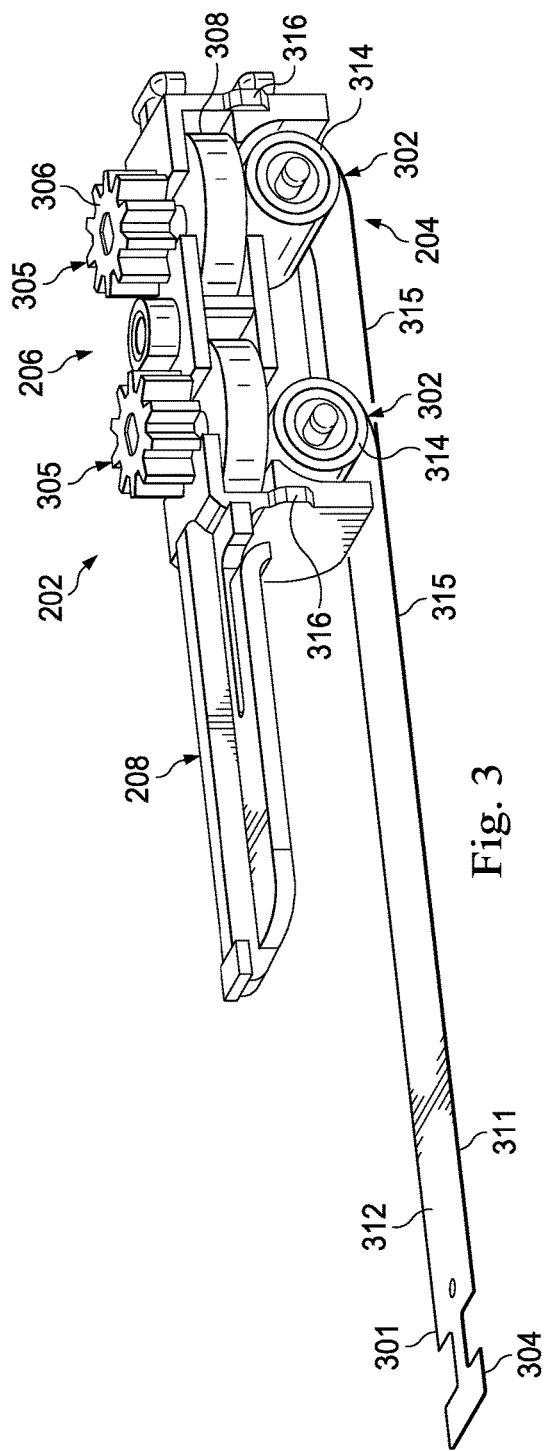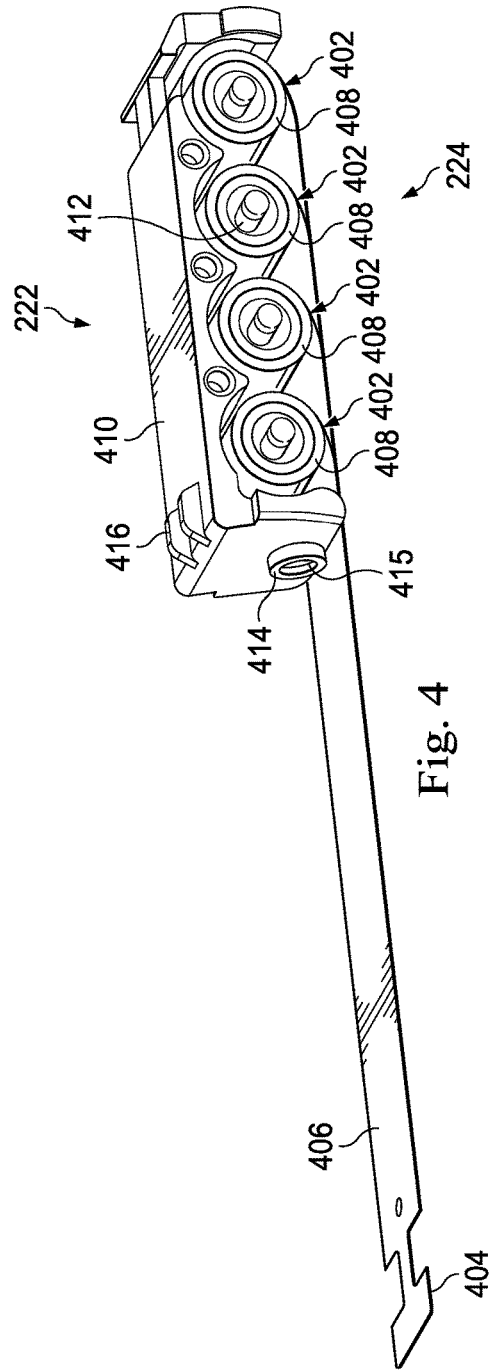

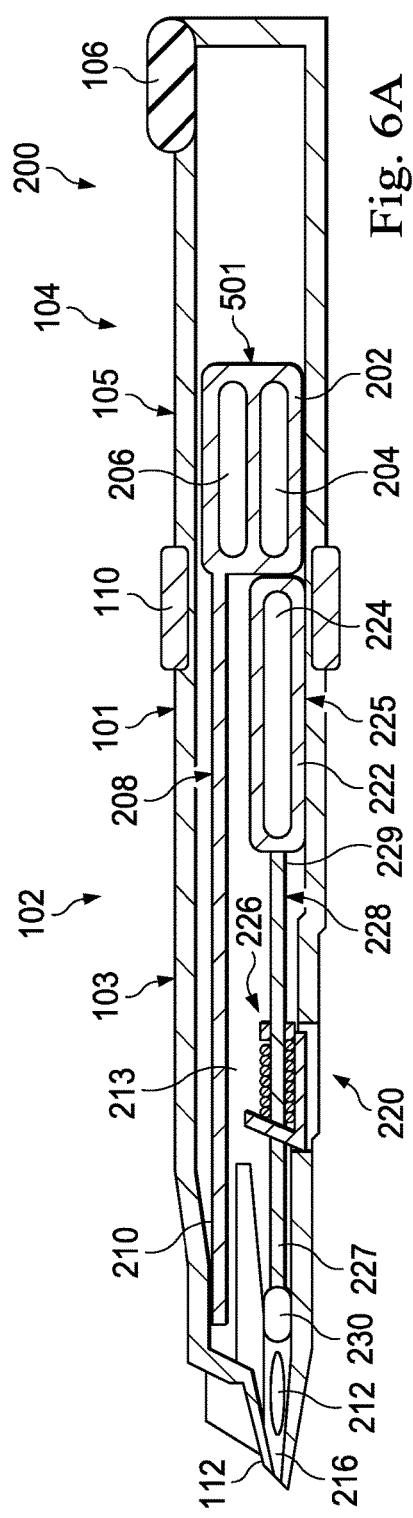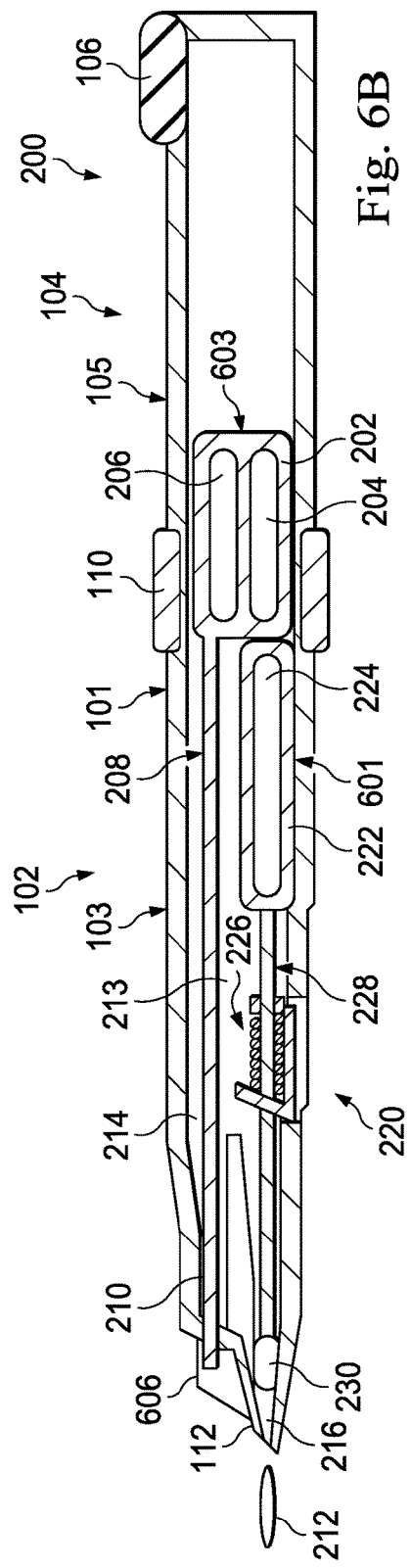

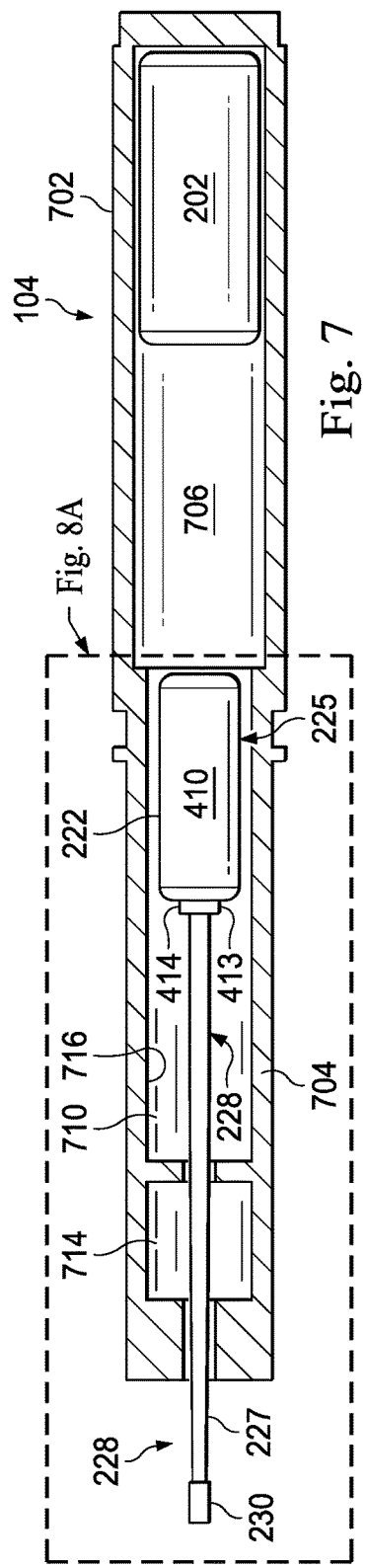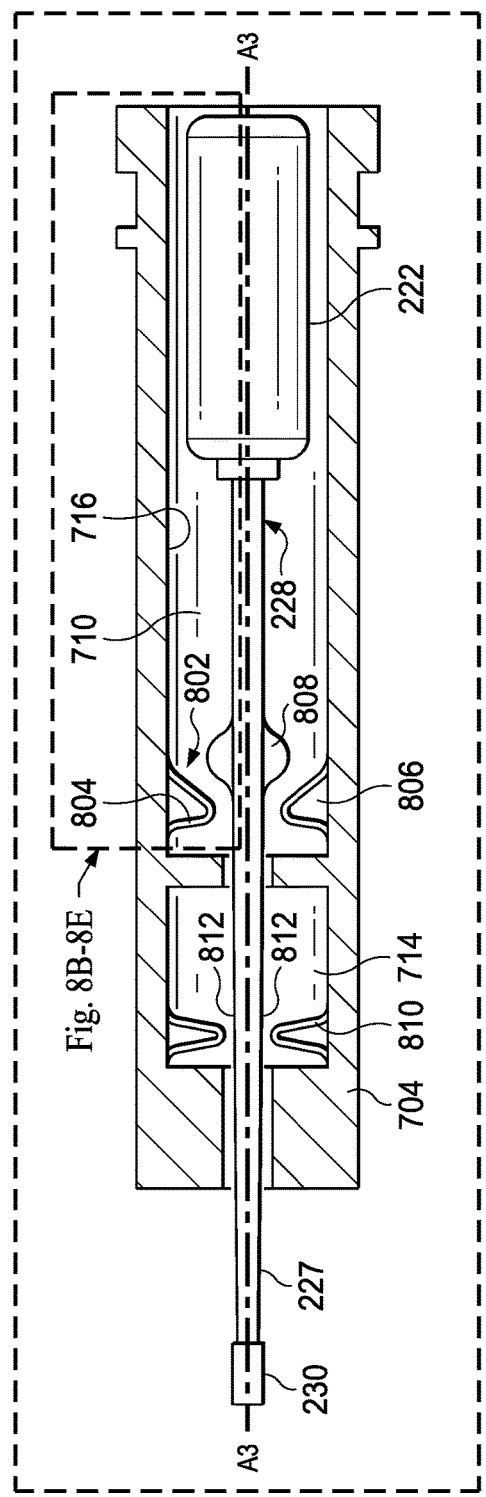

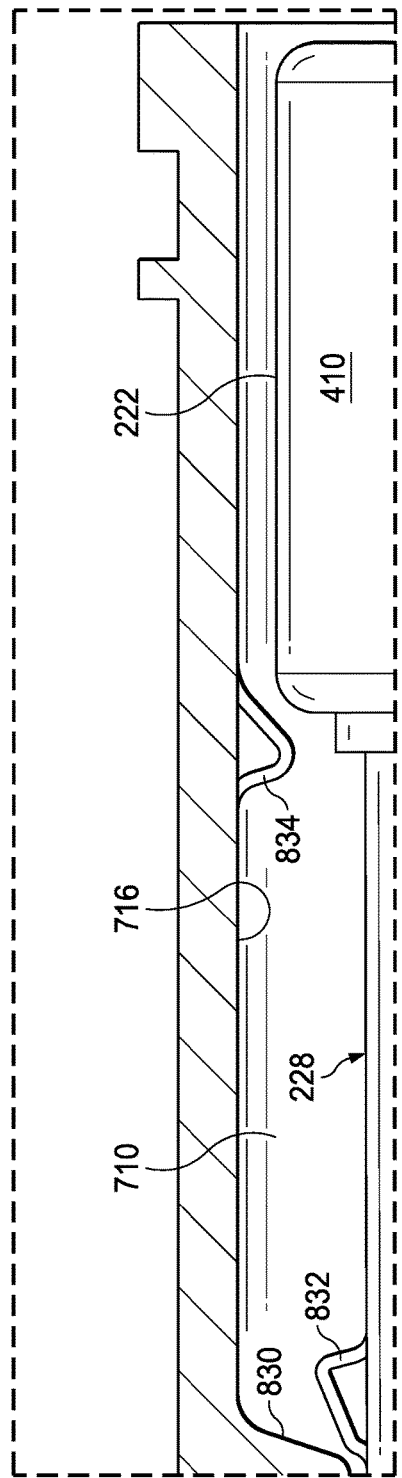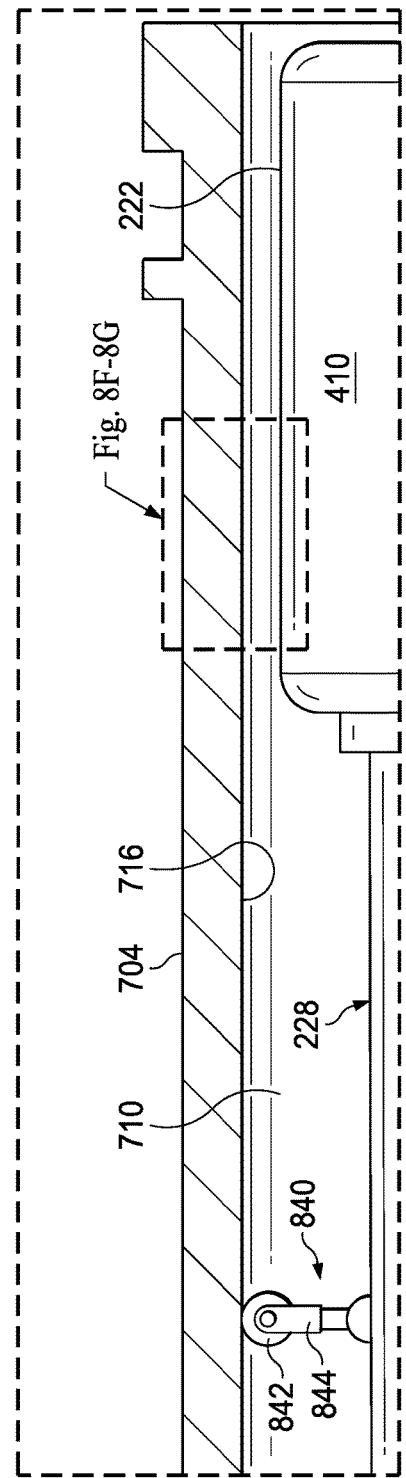

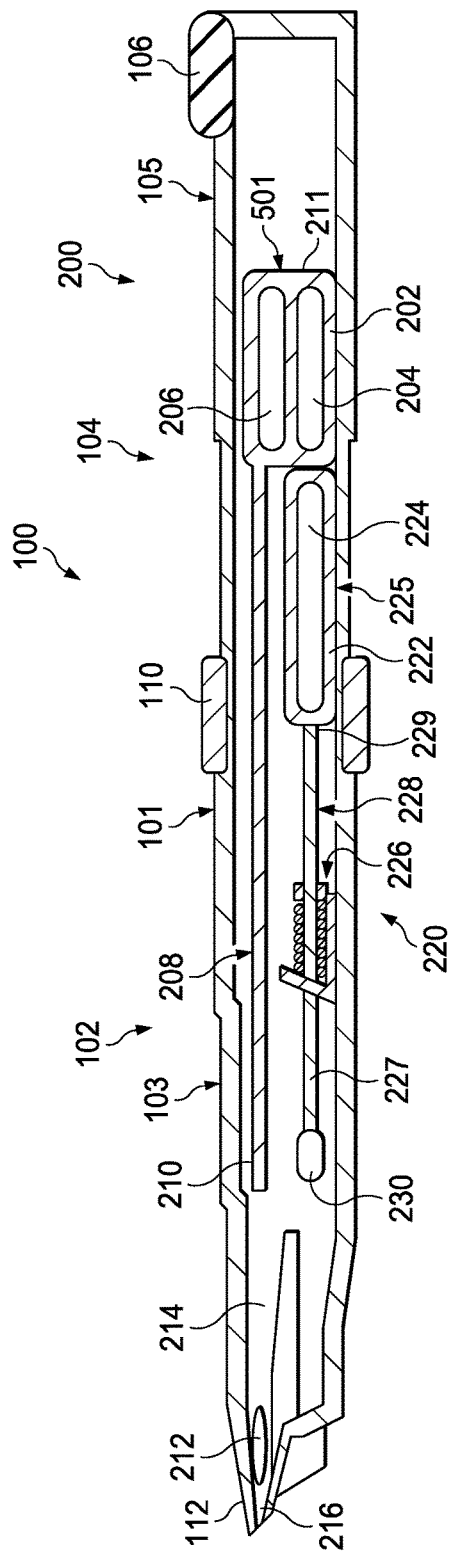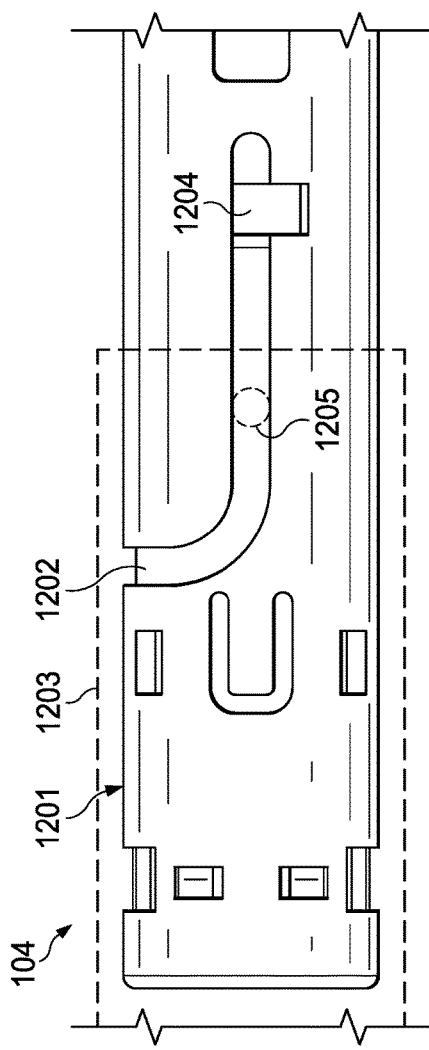
Fig. 11
Fig. 12

SYSTEMS AND METHODS FOR DEPLOYMENT DAMPING IN INTRAOCULAR LENS DEPLOYMENT

TECHNICAL FIELD

The present disclosure is directed to methods and systems for performing ophthalmic surgical procedures, and more particularly, to methods and systems for deploying an intraocular lens in an ophthalmic surgical procedure.

BACKGROUND

The human eye functions to provide vision by refracting light passing through a clear outer portion called the cornea and focusing the light by way of the lens onto the retina at the back of the eye. The quality of the visual image created by the focused light depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the natural lens and implantation of an artificial lens, typically referred to as an intraocular lens (IOL).

Insertion of an IOL is typically performed using an IOL insertion tool. A conventional IOL insertion tool includes an IOL insertion cartridge that may fold and insert the IOL through a relatively small incision into the eye. In some implementations, the IOL cartridge may include a folding chamber that has walls shaped to cause the IOL to fold in a desired manner as the IOL is moved through the chamber. Then, the folded IOL may be deployed into the patient's eye through the small incision. Typically, the operator of the IOL insertion tool manually pushes the IOL through the folding chamber by using a plunger that is engaged with the IOL. The operator also pushes the IOL out of the distal end of the IOL insertion tool and into the patient's eye. Because the IOL insertion tool is manually operated, the applied manual force may vary by operator and even by surgery. This variation in applied manual force can lead to undesirable folding results and improper IOL positioning within the eye, leading to inconsistent surgical outcomes. It is desirable to find methods and systems for providing improved and consistent advancement of the IOL through the folding and deployment of the IOL into the patient's eye.

SUMMARY

Consistent with some implementations, an intraocular lens (IOL) insertion apparatus may include a handpiece body having a distal tip, a deployment chamber formed within the handpiece body and forming an opening at a distal end of the handpiece body, and a deployment system disposed within the handpiece body. The deployment system may include a deployment carriage movable between a proximal position and a distal position within the handpiece body and a deployment plunger. The deployment plunger may include a shaft with a proximal end secured to the deployment carriage and a distal end to engage a folded IOL. The insertion apparatus may additionally include a damping feature protruding from a wall of the deployment chamber or a portion of the deployment system. The first damping feature may be positioned and arranged to increase resistance to movement of the deployment system along a portion of movement between the proximal position and the distal position.

The IOL insertion apparatus may also include a second damping feature extending outwardly from the other of the wall of the deployment chamber and a portion of the deployment system. The first damping feature may be disposed to make contact with the second damping feature as the deployment system moves. The second damping feature may extend outwardly from the deployment carriage of the deployment system. The second damping feature may include a wheel that contacts the wall of the deployment chamber. The second damping feature may extend outwardly from the shaft of the deployment plunger. The first damping feature may include at least one flexible spring structure. The first damping feature may be structurally arranged to provide a frictional engagement between the deployment chamber and the deployment system at a plurality of different positions between the initial proximal position and the final distal position. The first damping feature may be textured to provide the frictional engagement. The IOL insertion apparatus may also include a third damping feature protruding inwardly from the wall of the deployment chamber. The first damping feature may be disposed to contact a body of the deployment carriage as the deployment carriage moves towards the final distal position.

Consistent with some implementations, an IOL insertion apparatus may include a handpiece body having a distal tip, a deployment chamber formed within the handpiece body and having an opening located at a distal end of the handpiece body, and a lens deployment system disposed within the handpiece body. The deployment system may include a deployment carriage movable between a first position and a second position within the handpiece body and a deployment plunger including a shaft having a proximal end secured to the deployment carriage and a distal end to engage a lens during deployment thereof. The IOL insertion apparatus may further include a first damping feature protruding outwardly from the lens deployment system arranged to provide increased frictional resistance to movement of the deployment system during a portion of movement between an initial proximal and final distal positions.

The deployment carriage may include a spring system that biases the deployment carriage in a distal direction towards the final distal position. The first damping feature may include a contact wheel that contacts a portion of the deployment chamber and a hinged beam coupling the contact wheel to the lens deployment system. The hinged beam may include a hinge that is bendable to maintain contact between the contact wheel and an inner wall of the portion of the deployment chamber. The wheel may include one or more gears that provide resistance to the movement. The IOL insertion apparatus may also include a second damping feature protruding from an inner wall of a portion of the deployment chamber. The first damping feature and the second damping feature may contact each other during at least a portion of the movement of the deployment carriage to provide resistance to the movement of the deployment carriage. The IOL insertion apparatus may also include a third damping feature protruding from the inner wall of the portion of the deployment chamber. The third damping feature may be offset from the second damping feature along a central axis of the deployment chamber. The first damping feature may be rigid, and the second damping feature may be formed from a flexible membrane.

Consistent with some implementations, an IOL insertion apparatus may include a handpiece body having a proximal section and a distal section, a deployment carriage, and a first damping feature. The distal section of the handpiece body may be rotatable relative to the proximal section between a first rotational position and a second rotational position. The second rotational position may align a deployment plunger with an IOL deployment chamber. The deployment carriage may be connected to a proximal end of the deployment plunger and releasably secured within the handpiece body by a deployment button. The deployment carriage may include a first set of springs to bias the deployment carriage to move in a distal direction. The first damping feature may protrude inwardly from a wall of the IOL deployment chamber. The first damping feature may make contact with the deployment carriage or the deployment plunger during a portion of movement, as the deployment carriage moves in the distal direction to provide resistance to the movement.

The IOL insertion apparatus may also include an advancement plunger and an advancement carriage connected to a proximal end of the advancement plunger and releasably secured within the handpiece body by a trigger mechanism. The advancement carriage may include a second set of springs to bias the advancement carriage to move in the distal direction. The IOL insertion apparatus may also include a second damping feature protruding outwardly from the deployment carriage. The second damping feature may be disposed proximally from the first damping feature and positioned to contact the first damping feature when the deployment carriage moves from an initial proximal position to a final distal position.

Additional aspects, features, and advantages of the present disclosure will become apparent from the following detailed description.

BRIEF DESCRIPTION OF THE DRAWINGS

The accompanying drawings illustrate implementations of the devices and methods disclosed herein and together with the description, serve to explain the principles of the present disclosure.

FIG. 1 is a diagram showing an illustrative intraocular lens (IOL) insertion apparatus that provides automated deployment of an IOL.

FIG. 2 is a diagram showing a cross-sectional view of a portion of the IOL insertion apparatus that provides automated deployment of the IOL as shown in FIG. 1.

FIG. 3 is a perspective view of an illustrative advancement carriage for use in the IOL insertion apparatus.

FIG. 4 is a perspective view of an illustrative deployment carriage for use in the IOL insertion apparatus.

FIG. 6A is a diagram showing a cross-sectional view of the IOL insertion apparatus with a deployment plunger engaged with the IOL.

FIG. 6B is a diagram showing a cross-sectional view of the IOL insertion apparatus with the deployment carriage in a forward position.

FIG. 7 is a partially cross-sectioned top view diagram showing a shaft of the deployment plunger extending within the IOL insertion apparatus of FIG. 1.

FIGS. 8A, 8B, 8C, 8D, 8E, 8F, and 8G are partially cross-sectioned top view diagrams showing damping features of the deployment plunger according to various implementations of the IOL insertion apparatus of FIG. 1.

FIG. 11 is a cross-sectional view of the IOL insertion apparatus of FIG. 1 showing a proximal section longitudinally displaced from a distal section.

FIG. 12 illustrates a side-view of a guidance track formed in a proximal section of an example IOL insertion apparatus.

Figure 5:
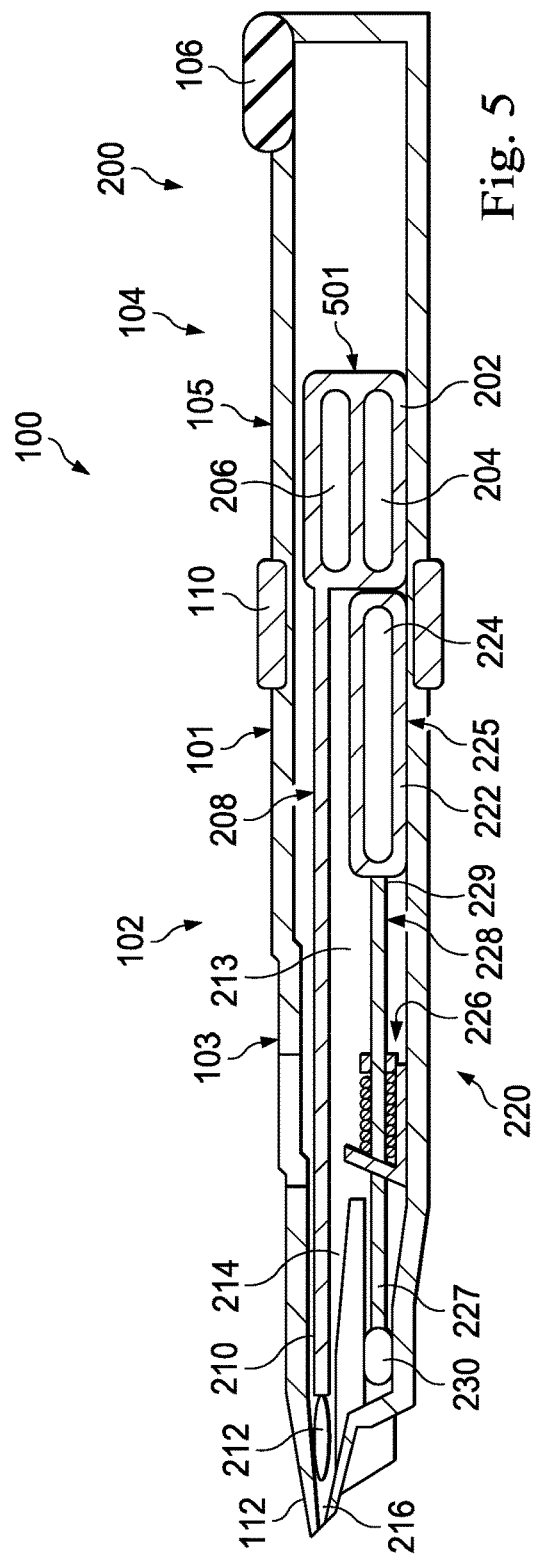
FIG. 5 is a diagram showing a cross-sectional view of the IOL insertion apparatus of FIG. 2 with the advancement carriage in a forward position.

These figures may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

According to principles described herein, an IOL insertion apparatus may provide automated deployment of the IOL into the patient's eye. In some implementations, advancement of the IOL through the folding chamber may be automated as well. Because of the controlled deployment of the IOL, the force applied on the plunger may be consistent and predictable, irrespective of the operator. Damping features may be included in the IOL insertion apparatus to compensate for difference in the insertion force required at different stages of the deployment. This may provide a higher percentage of properly inserted lenses than can be obtained with conventional systems. Furthermore, the automated deployment into the patient's eye may be self-contained within the IOL insertion tool and not rely on any external powering mechanism.

In some implementations of principles described herein, as the plunger of the IOL insertion apparatus moves, the plunger may contact one or more damping features that affect the velocity of the plunger during movement from an initial proximal position to a final distal position in order to maintain a more consistent velocity during advancement of the plunger. In the absence of such damping features, the movement before contact with the IOL may be faster than movement after contact with the IOL. Similarly, movement after deployment of the IOL (i.e., after the IOL passes beyond a distal tip of the deployment chamber) may be faster than the movement of the deployment plunger when pushing the IOL through the deployment chamber. The IOL insertion apparatus with automated, compensated advancement of the IOL is described in further detail below.

FIG. 1 is a diagram showing an illustrative intraocular lens (IOL) insertion apparatus 100 that provides automated deployment of an IOL. According to the present implementation, the IOL insertion apparatus 100 includes a handpiece body 101 having a distal section 102 with a distal tip 112 and having a proximal section 104. The distal section 102 includes a distal body 103 and the proximal section 104 includes a proximal body 105. The IOL insertion apparatus 100 also includes a set of release tabs 110 and includes an advancement trigger 106 that may be used by an operator to activate a plunger to fold an IOL in preparation for deployment.

The handpiece body 101 is arranged to be gripped by an operator such as a surgeon. Thus, the handpiece body 101 may be ergonomically shaped for gripping by hand. In some implementations, the IOL insertion apparatus 100 may be a single-use device that may be discarded after the IOL within the IOL insertion apparatus 100 has been inserted into the patient's eye.

As noted, the advancement trigger 106 may be used to initiate movement of the IOL through a folding chamber to fold the IOL. In the illustrated implementation, the advancement trigger 106 is a release button that permits movement of components that force the IOL through the folding chamber. In some implementations, the folding process, which includes advancement of the IOL through the folding chamber, may be automated. In such an implementation, an operator may trigger the folding process by pressing the advancement trigger 106.

The release tabs 110 may be used to release the proximal section 104 from the distal section 102. As will be described in further detail below, the proximal section 104 may be moved away from the distal section 102, rotated approximately 180 degrees, and then moved back towards the distal section 102. As shown by the arrow A1 in FIG. 1, the rotation may be clockwise or counterclockwise about a longitudinal axis A2 of the IOL insertion apparatus 100. This motion permits the folding process to be performed and then prepares the IOL insertion apparatus 100 for the deployment process after the folding process is completed, by aligning a deployment plunger (see FIG. 2) with a distal chamber. The folding chamber may be a portion of a deployment chamber that also includes the distal chamber. The deployment process involves moving the IOL outside of the distal tip 112 of the IOL insertion apparatus 100 and into the anterior segment of the patient's eye.

FIG. 2 is a diagram showing a cross-sectional view of a portion of the IOL insertion apparatus 100 of FIG. 1 that provides automated advancement and deployment of the IOL. The cross-sectional view illustrates an advancement system 200 that includes an advancement carriage 202 and an advancement plunger 208. The cross-sectional view also shows a deployment system 220 that includes a deployment carriage 222 and a deployment plunger 228, which extends within a portion of a deployment chamber 213. The deployment plunger 228 may be in the form of or include an elongated shaft. The cross-sectional view also shows an IOL 212 and the folding section 214. The folding section 214 is aligned with and coupled to the distal section 216. The folding section 214 and the distal section 216 form a distal region of the deployment chamber 213. Sidewalls, which may include a roof and floor, of the folding section 214 may be arranged to fold the lens of the IOL as well as haptics of the IOL prior to deployment from the distal section 216. In some implementations, the distal section 216 may define a cavity that narrows from a larger cross-section size to a smaller cross-sectional size in the distal direction.

According to the present implementation, the advancement carriage 202 is secured at a proximal position 201 within the handpiece body 101. The advancement carriage 202 may include a spring system 204 and a damping system 206. The spring system 204 applies a biasing force to the advancement carriage 202 that urges the advancement carriage 2020 to move toward the distal end of the IOL insertion apparatus 100. The advancement carriage 202 is restricted from moving due to the biasing force applied by the spring system 204 when the advancement carriage 202 is in a secured configuration. The advancement carriage 202 may remain secured at the proximal position 201 until the advancement carriage 202 is released from the proximal position 201, such as when an operator uses the advancement trigger 106. In the illustrated example, actuation of the advancement trigger 106 releases the advancement carriage 202 from the proximal position 201. Once released from the proximal position 201, the advancement carriage 202 moves in a distal direction due to the biasing force provided by the spring system 204. The distal movement of the advancement carriage 202 may be controlled by the damping system 206.

Distally-directed motion of the advancement carriage 202 causes corresponding motion of the advancement plunger 208. In the illustrated example, the advancement plunger 208 is an elongated structure that has a proximal end secured to the advancement carriage 202. The advancement plunger 208 has a distal end 210 configured to engage the IOL 212 to facilitate folding thereof. The advancement plunger 208 may be supported and guided as the advancement plunger 208 moves by a number of support and guidance structures (not shown).

In some implementations, the distal end 210 of the advancement plunger 208 may be substantially rigid. Thus, the rigid distal end 210 may more efficiently engage the IOL 212 to push the IOL 212 through the folding section 214. After the IOL 212 passes through the folding section 214, the IOL 212 is moved into the distal section 216 near the distal tip 112 of the distal section 102. The distal section 216 of the deployment chamber 213 may narrow toward a distal end thereof. Because the rigid distal end 210 of the advancement plunger 208 may not be compressible in some implementations, the distal end 210 of the advancement plunger 208 may be prevented from extending into the narrowing region of the distal section 216. For example, in some instances, a size of the distal end 210 may exceed the size of a portion of the narrowing region of the distal section 216, preventing further advancement of the advancement plunger 208 and advancement carriage 202.

According to the illustrated implementation, the deployment carriage 222 is secured within the handpiece body 101 at an initial proximal position 225 that is located distal to the advancement carriage 202. In the illustrated example, the deployment plunger 228 is attached to the deployment carriage 222. The deployment plunger 228 may be attached to the deployment carriage 222 by a boss extending from the carriage 222 and having a recess configured to receive a proximal end 229 of the deployment plunger 228. In other implementations, the deployment carriage 222 and the deployment plunger 228 may be integrally formed. In still other implementations, the deployment carriage 222 and the deployment plunger 228 may be adjoined in any desired manner. The deployment plunger 228 has a proximal end 229 and is connected to the deployment carriage 222 at the proximal end 229. The deployment plunger 228 also includes a distal portion 227 having a compressible tip 230.

FIG. 2 illustrates the advancement plunger 208 positioned to engage the IOL 212 to push the IOL 212 through the remainder of the distal section 216 and further out of the IOL insertion apparatus 100. However, as will be described in further detail below, the IOL insertion apparatus 100 can be reconfigured to rotate the deployment plunger 228 around the axis A2 and into position to engage the IOL 212 after the IOL 212 is folded. When the deployment plunger 228 is positioned to engage the IOL 212, pressing or otherwise actuating the deployment button 226 causes the deployment plunger 228 to move distally to push the IOL 212 out of the distal section 216 at the distal tip 112.

In some implementations, the deployment carriage 222 may include a spring system, such as the spring system 224 shown in FIG. 2. The spring system 224 applies a biasing force to the deployment carriage 222 that biases the deployment carriage 222 toward the distal end of the IOL insertion apparatus 100. The deployment carriage 222 may remain at the proximal position 225 until the deployment carriage 22 is released. In the illustrated example, the deployment carriage 222 is released from the proximal position 225 by actuation of the deployment button 226. For example, an operator may press the deployment button 226, causing the deployment carriage 222 to be released from the proximal position 225. Once released, the biasing force applied by the spring system 224 causes the deployment carriage 222 and deployment plunger 228 to move distally.

In some implementations, the deployment button 226 may not be exposed until the deployment plunger 228 is positioned to engage the IOL 212. For example, in some implementations, the deployment button 226 may not be exposed until the distal section 102 and the proximal section 104 have been rotated about 180 degrees relative to one another. Maintaining the deployment button 226 in an unexposed condition until the deployment plunger 22 is positioned to engage the IOL 212 may prevent an operator from inadvertently activating the deployment carriage 222 before activating the advancement carriage 202 and reconfiguring the distal and proximal sections 102 and 104 of the IOL insertion apparatus 100. Upon pressing the deployment button 226, the deployment carriage 222 may move distally until reaching a hard stop or until the operator discontinues pressing the deployment button 226. Distally directed movement of the deployment carriage 222 causes corresponding movement of the deployment plunger 228. As will be described in further detail below, this movement of the deployment plunger 228 moves the IOL 212 out of the distal section 216 and, ultimately, out of the IOL insertion apparatus 100. Generally, the IOL 212 is expelled from the IOL insertion apparatus 100 and into a patient's eye.

As illustrated, the deployment plunger 228 has a tip 230 that is made of a compressible material. Thus, when the deployment plunger 228 engages the IOL 212, the tip 230 may be compressed to pass through the narrowing region of the distal section 216 so as to move the IOL 212 out of the IOL insertion apparatus 100 and into the patient's eye. At the end of the movement of the carriage 222, the tip 230 may be positioned beyond the distal section 216 and outside of the IOL insertion apparatus 100.

FIG. 3 is a perspective view of an illustrative advancement carriage 202 for use in the IOL insertion apparatus 100 of FIGS. 1 and 2. As described above, some implementations of the advancement carriage 202 may include a spring system 204 and a damping system 206. Other implementations of the advancement carriage 202 may not include one or more springs to generate the biasing force. Rather, in some implementations, the IOL insertion apparatus 100 may include some other mechanism, such as a compressed gas, to force the advance carriage 202 toward the distal tip 112. In the illustrated example, the spring system 204 includes one or more biasing elements such as springs 302. In the illustrated example, the springs 302 are constant force springs. A constant force spring is one in which the force applied by the spring remains constant despite the position of the spring. In other words, a constant force spring does not follow Hooke's law. In some embodiments, the springs 302 may not be constant force springs but, rather, may provide a non-constant force. Such a non-constant force may be compensated or modulated by the damping system 206 so that the force placed on the advancement plunger 208 may be substantially constant. The example spring system 204 includes two springs 302. However, in other implementations, the spring system 204 may include fewer or additional springs.

In the illustrated example, each of the constant force springs 302 includes a coil 314 having an unrolled portion 315, a pickup portion 312 distal of the unrolled portion 315, and a mounting tab 304 at a distal end 301. In one implementation, the coils 314 are formed from rolled-up, elongated metal sheets 311. The sheets 311 may be biased to the rolled-up position. Thus, when the sheets 311 are unrolled or extended as represented by the unrolled portion 315, the sheets 311 are biased to revert back to a rolled-up state absent any structure or force preventing the sheets 311 from doing so. The mounting tab 304 (only one is visible in FIG. 3) may be disposed at the distal end 301 and may be structurally configured to be secured to an interior of the handpiece body 101. The pickup portion 312 may be a portion of the sheet disposed between the distal end 301 and the unrolled portion 315 and may not have spring-like properties. The pickup portion 312 may provide for ease of assembly and may maintain a substantially flat profile within the space between the advancement carriage 202 and the location to which the mounting tab 304 is secured. When the advancement carriage 202 is released, the unrolled portion 315 rolls-up to form a part of the coil 314 of the constant force spring 302, thus moving the advancement carriage 202 in the distal direction toward the mounting tab 304. While the illustrated advancement carriage 202 shown in FIG. 3 includes only two constant force springs 302, other embodiments may include only one constant force spring or more than two constant force springs. In the example shown in FIG. 3, the pickup portions 312 of the constant force springs 302 overlap each other, and the constant force springs 302 cooperate together to bias the advancement carriage 202 toward the mounting tab 304 and toward the distal tip 112 of the IOL insertion apparatus 100.

The damping system 206 helps control the speed of the distal movement of the advancement carriage 202 after the advancement carriage 202 has been released. In other words, the damping system 206 prevents the advancement carriage 202 from moving too fast once released by the advancement trigger (e.g., advancement trigger 106 shown in FIG. 1). In the illustrated example, the damping system 206 includes a plurality of rotary dampers 305. The rotary dampers 305 may include a body 308 and a pinion 306. In some implementations, the body 308 may be an injection molded body 308. The body 308 may include a viscous fluid, a rotor (not shown), and a stator (not shown). The rotary damper 305 may provide fluid damping through the shearing force of the fluid resistance between the surfaces of the rotor and stator.

In this implementation, the pinion 306 may include a number of teeth that are configured to engage a rack (not shown) that may extend along an inner surface of the handpiece body 101. As such, when the advancement carriage 202 advances, the rack rotates the pinion 306, which in turn rotates the rotor in the viscous fluid in the body 308, thereby dampening the forward movement of the advancement carriage 202. While the present example illustrates two rotary dampers 305, other embodiments may include a single rotary damper or more than two rotary dampers.

The advancement carriage 202 also includes tabs 316. Although only two tabs 316 are illustrated, additional tabs 316 may also be provided on the opposite side of the advancement carriage 202. Thus, in some implementations, the advancement carriage 202 may include four tables 316. However, the scope of the disclosure is not so limited. Rather, the advancement carriage 202 may include fewer tabs. For example, in some implementations, the advancement carriage 202 may include a single tab 316 on each side thereof. In other implementations, the advancement carriage 202 may include more than two tabs 316 on a side thereof.

Figure 10:
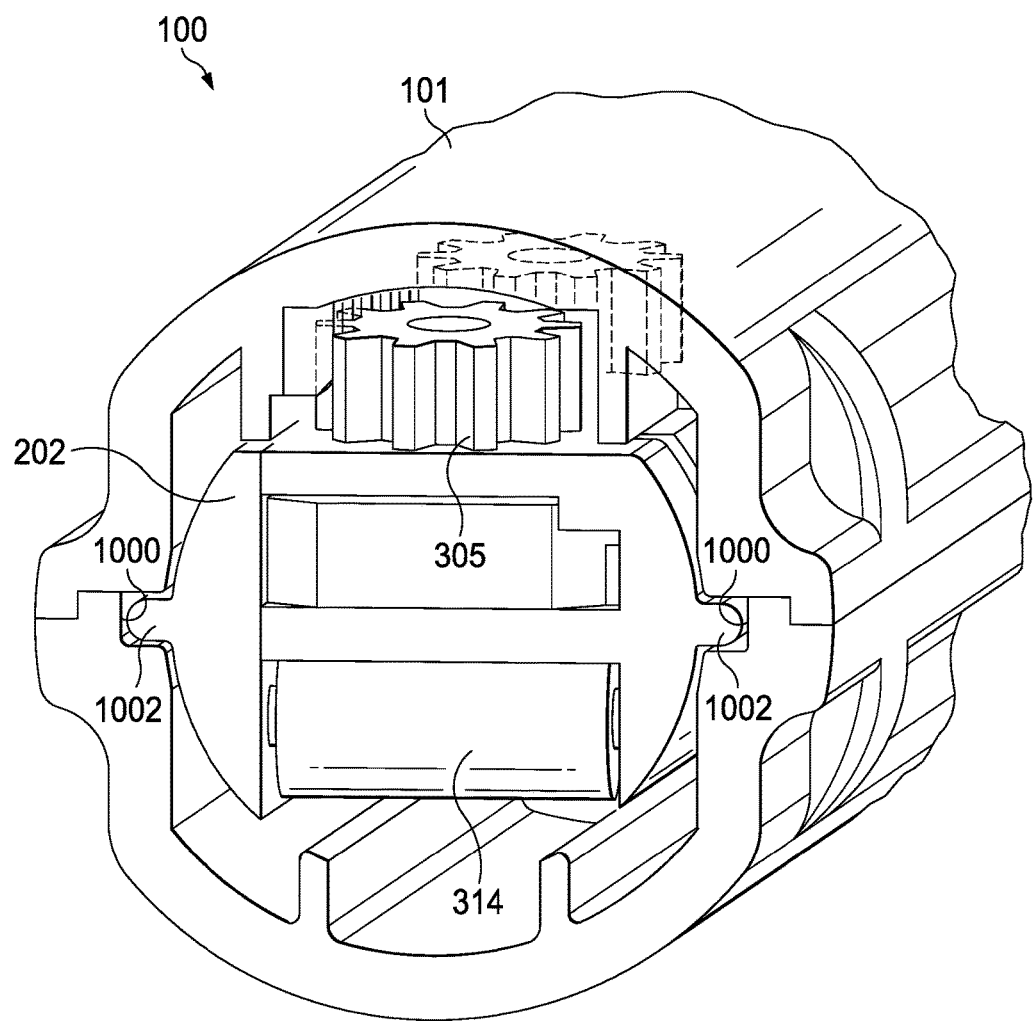
FIG. 10 is a cross-sectional view of the example IOL insertion apparatus of FIG. 1 showing the advancement carriage with tabs received into grooves formed within a handpiece body of the IOL insertion apparatus.

The tabs 316 are received into grooves formed into in the handpiece body 101. For example, FIG. 10 shows grooves 1000 formed into the handpiece body 101. In other implementations, one or more of the grooves 1000 may be defined by or formed in another component disposed within the IOL insertion handpiece 100. In the illustrated example, the advancement carriage 202 includes tabs 1002 that are received into the grooves 1000. In some instances, the tabs 1002 extend along only a portion of a length of the advancement carriage 202. In other implementations, the tabs 1002 may extend along an entire length of the advancement carriage 202. Still further, although FIG. 10 shows only two tabs 1002, in other implementations, the advancement carriage 202 may include more than two tabs 1002 or less than two tabs 1002. The interaction between the grooves 1000 and the tabs 1002 keeps the advancement carriage 202 properly aligned and positioned within the IOL insertion device 100 as the advancement carriage 202 is advanced, as shown, for example, in FIG. 10. The tabs 316 cooperate with the grooves to control an orientation and advancement of the advancement carriage 202 as the advancement carriage 202 advances through the handpiece body 101.

FIG. 10 shows the grooves 1000 in the context of the advancement carriage 202. However, one or more grooves similar to grooves 1000 may be used in the context of the deployment carriage 222. In such implementations, the tabs 316 formed on or otherwise coupled to the deployment carriage 222 may be received into corresponding groove, which may be similar to grooves 1000. In still other implementations, the tabs of the deployment carriage 222 may be similar to those shown in FIG. 10 and described above.

FIG. 4 is a perspective view of an illustrative deployment carriage 222 for use in the IOL insertion apparatus 100 of FIGS. 1 and 2. According to the present implementation, the spring system 224 of the deployment carriage 222 includes four constant force springs 402. In some implementations, the deployment carriage 222 may include fewer or more than four constant force springs 402. Like the constant force springs 302 described, the constant force springs 402 include a coil 408, a pickup portion 406, and a mounting tab 404. In the depicted implementation, the pickup portion 406 overlap each other and the constant force springs 402 cooperate together to bias the deployment carriage 222 toward the mounting tab 404 and toward the distal tip 112 of the IOL insertion apparatus 100.

The constant force springs 402 may be secured to a carriage body 410 by mounting posts 412. In some implementations, a boss 414 may be disposed on a distal end of the carriage body 410. The boss 414 may include an opening 415 configured to receive a shaft of the deployment plunger 228 as shown in FIG. 2. Implementations of the carriage body 410 may include one or more protruding features 416. One or more protruding features 416 may be inserted into guide channels used to guide the deployment carriage 222 as the deployment carriage 222 travels from the initial, proximal position 225 to a final distal position. The guide channels may be formed in the handpiece body 150, for example. In other implementations discussed in more detail below, one or more of the protruding features 416 or other similar protruding features may function as damping features that provide resistance to the distally directed movement of the carriage 222 during deployment of the IOL 212. In such implementations, one or more of the protruding features 416 may make contact with an inner wall of the deployment chamber 213 and/or make contact with another damping feature protruding inwardly therefrom.

FIG. 5 is a diagram showing a cross-sectional view of the IOL insertion apparatus 100 with the advancement carriage 202 in a distal position 501. As described above, the advancement trigger 106 may be used to release the advancement carriage 202 from the proximal position 201 as illustrated in FIG. 2. After being released, the spring system 204 and the damping system 206 of the advancement carriage 202 cooperate to move the advancement carriage 202 distally at a controlled rate. The advancement plunger 208 moves distally with the advancement carriage 202 to move the IOL 212 through the folding section 214 and into the distal section 216 of the deployment chamber 213. Ultimately, the advancement carriage 202 is stopped in the distal position 501. In some implementations, the advancement carriage 202 may be physically prevented from moving any further in the distal direction after reaching the distal position 501. In some implementations, the advancement carriage 202 may be prevented from moving further because of contact with the deployment carriage 222, which may be releasably secured in the depicted position. In other words, the distal position 501 of the advancement carriage 202 may correspond to the location at which the advancement carriage 202 engages the deployment carriage 222.

FIG. 6A is a diagram showing a cross-sectional view of the IOL insertion apparatus 100 with the deployment plunger 228 aligned with the IOL 212. In other words, the distal section 102 (as shown in FIG. 1) has been rotated with respect to the proximal section 104 (as shown in FIG. 1) such that, instead of the advancement plunger 208 being aligned with the IOL 212, the deployment plunger 228 is now aligned with the IOL 212. In some implementations, the distal section 102 may be released from the proximal section 104 through use of the release tabs 110. In some implementations, the release tabs 110 are physically prevented from releasing the proximal section 104 from the distal section 102 until the advancement carriage 202 has moved into the distal position 501. Preventing the release tabs 110 from being released in this manner may help to ensure that the IOL 212 is moved into the appropriate position within the distal section 216 before the advancement plunger 208 is removed from engagement with the IOL 212. Thereafter, the deployment plunger 228 may be placed into position such that a distal portion 227 of the deployment plunger 228 is within the folding section 214 of the deployment chamber 213 and prepared for engagement with the IOL 212.

Consequently, the operator may move the IOL 212 from alignment with the advancement plunger 208 and into alignment with the deployment plunger 228. FIG. 11 is a diagram showing a cross-sectional view of the IOL insertion apparatus 100 with the proximal section 104 longitudinally displaced from the distal section 102. After the advancement carriage 202 has been moved to the distal position 501, an operator releases the proximal section 104 from the distal section 102. In some implementations, the operator releases the proximal section 104 from the distal section 102 with the use of the release tabs 110. The proximal section 104 is then moved away from the distal section 102. In some examples, as will be described in further detail below, a guidance track may be used to guide the proximal section 104 as it is moved away from the distal section 102. The proximal section 104 may be slidingly engaged with the distal section 102 such that, as the operator moves the proximal section 104 away from the distal section 102, a region of the proximal body 105 slides along a region of the distal body 103. The operator moves the proximal section 104 at least a predefined distance away from the distal section 102 such that the advancement plunger 208 and the deployment plunger are clear of the folding section 214. The distal section 102 (containing the folded IOL 212) is rotated relative to the proximal section 104 (containing both the advancement plunger 208 and deployment plunger 228) such that the deployment plunger 228 is aligned with the folding section 214, the distal section 216, and the IOL 212.

In some implementations, the proximal section 104 may be rotated about 180 degrees relative to the distal section 102. The operator may then move the proximal section 104 towards the distal section 102 to a point where the proximal section 104 reconnects with the distal section 102. Reconnection of the proximal section 104 with the distal section 102 causes the tip 230 of the deployment plunger 228 to pass through the folding section 214 for engagement with the IOL 212 positioned within the distal section 216.

To aid the operator with moving and rotating the proximal section 104 with respect to the distal section 102, the proximal body 105 and the distal body 103 may include guidance features, such as, for example and without limitation, a track. For example, the distal body 103 may include a track while the proximal body 105 may include a protrusion that fits within the track. Conversely, the proximal body 105 may include a track while the distal body 103 may include a protrusion. Other arrangements are also contemplated.

FIG. 12 illustrates a side-view of a guidance track 1202 formed in the proximal section 104 of the IOL insertion apparatus 100, according to some implementations. FIG. 12 illustrates an example in which the distal end 1201 of the proximal body 105, shown in FIG. 1, includes a guidance track 1202. The distal end 1201 may be generally covered by a proximal end 1203 of the distal body 103, shown in FIG. 1, when the IOL insertion apparatus 100 is fully assembled. Thus, the guidance track 1202 is generally not visible to an operator of the assembled IOL insertion apparatus 100. The distal body 103 may include a pin 1205 that fits within the guidance track 802. In some instances, the pin 1205 may be formed in the proximal end 1203 of the distal body 103. The guidance track 1202 guides the pin 1205 and thus the proximal section 104 as the proximal section 104 is moved and rotated relative to the distal section 102, as shown in FIG. 1. In some implementations, the guidance track 1202 may be substantially U-shaped and positioned along the proximal body 105 in a manner such that parallel portions of the U-shaped guidance track 1202 extend longitudinally along the IOL insertion apparatus 100.

After the proximal section 104 has been rotated relative to the distal section 102 and the deployment plunger 228 has been aligned with the IOL 212, the deployment button 226 may be exposed for use by an operator. In some implementations, while the advancement plunger 208 is aligned with the IOL 212, a portion of the proximal body 105 may cover the deployment button 226 so that the deployment button 226 is not able to be pressed or, in some instances, even seen by the operator. With the deployment button 226 covered by the proximal body 105, the operator is prevented from inadvertently triggering the deployment process before the deployment plunger 228 is aligned with the IOL 212.

Figure 13A:
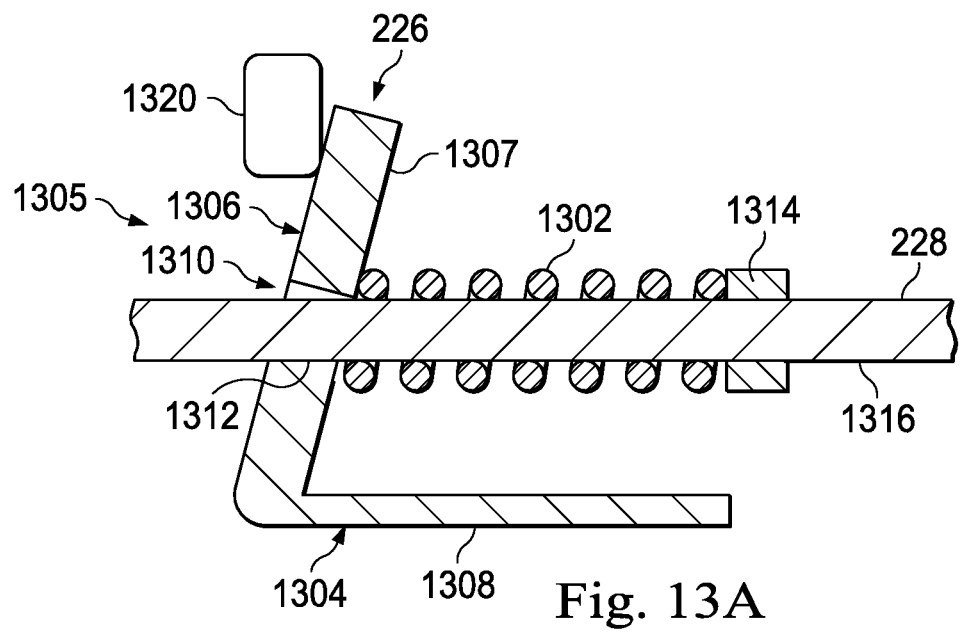
FIG. 13A is a diagram showing an illustrative deployment trigger in an unengaged state and a portion of the deployment plunger.
Figure 13B:
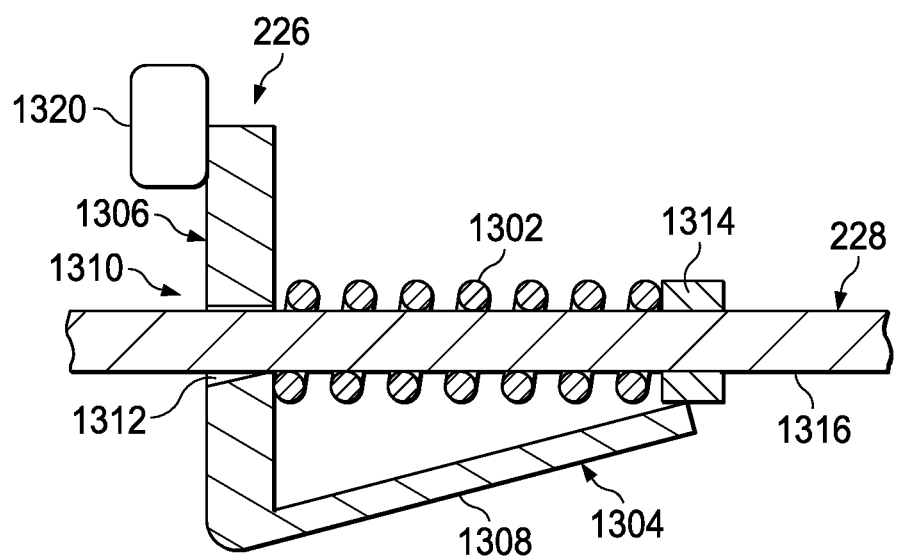
FIG. 13B is a diagram showing the deployment trigger of FIG. 13A in an engaged state along with the portion of the deployment plunger.

FIG. 13A is a diagram showing an illustrative deployment trigger 226 in an unengaged state and a portion of the deployment plunger 228. FIG. 13B is a diagram showing the deployment trigger 226 in an engaged state with the portion of the deployment plunger 228. According to the present example, the deployment trigger 226 includes a spring-loaded cleat 1305. The cleat 1305 includes a first portion 1306 and a second portion 1304. In this implementation, the first portion 1306 is angled substantially transverse to the second portion 1304. The cleat 1305 is spring-loaded in the distal direction such that the end portion 1307 of the first portion 706 is pressed against a hard stop 1320. The hard stop 1320 thus acts as a pivot point for the cleat 1305. When the deployment trigger 226 is not engaged, the cleat 1305 is in a locked state as shown in FIG. 13A. Conversely, when the deployment trigger 226 is engaged, by an operator for example, the cleat 1305 is in an unlocked state as shown in FIG. 13B.

The first portion 1306 includes a tapered through-hole 1310 sized and shaped to allow the deployment plunger 228 to pass therethrough. The through-hole 1310 includes a gripping surface 1312 forming an interior surface of the through-hole 1310. Selective contact between the gripping surface 1312 and the deployment plunger 228 allows the operator to permit or prevent advancement of the deployment plunger 228 relative to the cleat 1305. In the implementation shown, the gripping surface 1312 is substantially aligned with an outer surface 1316 of the deployment plunger 228 when the deployment trigger 226 is the unengaged state. This maximizes the contact area between the gripping surface 1312 and the outer surface 1316 of the deployment plunger 228. Thus, when the deployment trigger 228 is not engaged, the cleat 1305 grasps the surface 1316 of the deployment plunger 228 to prevent distal movement of the deployment plunger 228. In other words, when in the trigger 228 is in the unengaged state, the cleat 1305 locks the deployment plunger 228 in place.

A compression spring 1302 may bias the cleat 1305 to the locked position shown in FIG. 13A. In this implementation, the compression spring 1302 extends between the first portion 1306 of the cleat 1305 and a stop surface 1314. The stop surface 1314 may be secured to the interior of the handpiece body (e.g., handpiece body 101 shown in FIG. 1).

In this implementation, the second portion 1304 includes an actuation surface 1308. In some implementations, the actuation surface 1308 may be ergonomically designed for an operator's thumb or finger to depress or otherwise move. Pressing the actuation surface 1308 causes the cleat 1305 to rotate about the hard stop 1320 to change the angle of the through-hole 1310 relative to the deployment plunger 228 such that the gripping surface 1312 no longer fully grips the surface 1316 of the deployment plunger 228. Pressing the actuation surface 1308 causes the compression spring 1302 to compress. Pivoting the cleat 1305 as a result of pressing the actuation surface 708 releases the deployment plunger 228 to be moved distally by the spring systems 204, 224 of the advancement carriage 202 and the deployment carriage 222. In other words, the cleat 1305 is no longer locked with the deployment plunger 228.

In some implementations, the operator may release the deployment trigger 226 any time during forward motion of the deployment plunger 228 before the deployment carriage 222 reaches its final distal position 601. This allows the compression spring 1302 to return the cleat 705 from the unlocked state of FIG. 13B to the locked state of FIG. 13A. By doing this, the user is able to interrupt the automated deployment process by simply releasing the deployment trigger 226. The operator may continue the automated deployment process by re-pressing the deployment trigger 226

FIG. 6B is a diagram showing a cross-sectional view of the IOL insertion apparatus 100 with the deployment carriage 222 in a distal position. According to the present implementation, when the deployment button 226 is depressed or otherwise actuated, the deployment carriage 222 is released. In some implementations, actuation of the button 226 releases a latch that secures the deployment carriage 222 in the proximal position 225. Thus, the spring system 224 of the deployment carriage 222 causes the deployment carriage 222 to move in the distal direction, causing corresponding movement of the deployment plunger 228 to move the IOL 212 out of the distal section 216 of the deployment chamber 213. Accordingly, in some implementations, the biasing force generated by the spring system 224 is sufficient to advance the deployment plunger 228 and deploy the IOL 212 out of the IOL insertion apparatus 100.

In some implementations, the advancement carriage 202 may also help move the deployment plunger 228 forward. As described above, the advancement carriage 202 may be prevented from moving further when it first engages the deployment carriage 222. Thus, when the deployment carriage 222 is released from the proximal position 225 and caused to move distally as a result of the biasing force generated by the spring system 224, the biasing force generated by the spring system 204 of the advancement carriage 202 may also assist in moving the deployment plunger 228 distally. Accordingly, in some implementations, the combined forces provided by the spring system 224 of the deployment carriage 222 and the spring system 204 of the advancement carriage 202 may provide a force sufficient to move the tip 230 of the deployment plunger 228 through the narrowing region of the distal section 216 and deploy the IOL 212 out of the IOL insertion apparatus 100. In other implementations, the spring system 224 of the deployment carriage 222, alone, supplies the force needed to deliver the IOL 212 from the distal section 216 and out of the IOL insertion apparatus 100. As described above, the tip 230 may be made of a compressible material that compresses so as to conform to a cross-sectional shape of the distal section 216 as the tip 230 passes through the distal section 216.

Eventually, the deployment carriage 222 reaches a final distal position 601 and the advancement carriage 202 reaches a final distal position 603. With the advancement carriage 202 located at the final distal position 603, the distal end 210 of the advancement plunger 208 may be located within a forward chamber 606. The forward chamber 606 may be sized and shaped to accommodate the distal end 210 of the advancement plunger 208. The forward chamber 606 may thus provide space for the distal end 210 of the advancement plunger 208 to prevent the advancement carriage 202 from being prematurely stopped in implementations in which the advancement carriage 202 contributes to the movement of the deployment plunger 228. Although FIG. 6B illustrates the tip 230 as being disposed within the distal section 216 with the deployment carriage 222 located at final distal position 601, in some implementations, the tip 230 of the deployment plunger 228 may extend beyond the distal tip 112 and be located outside of the handpiece body 101.

In some implementations, the deployment button 226 is designed such that, in an unpressed state, the deployment button 226 grips the deployment plunger 228 to prevent distal movement of the deployment plunger 228. However, when the deployment button 226 is pressed, the deployment plunger 228 is released and allowed to move forward.

FIG. 7 illustrates a partial cross-sectioned top view of the proximal section 104 of the IOL insertion apparatus 100. In the illustrated example, the proximal section 104 includes a proximal portion 702 and a distal portion 704. The distal portion 704 may be sized to fit within the distal section 103 as illustrated in FIG. 1. Accordingly, a size of the distal portion 704 may be smaller than a size of the proximal portion 702. In some implementations, a cross-sectional shape of the proximal section 104 may be generally circular in shape. As such, in some implementations, a diameter of the distal portion 704 may be smaller than a diameter of the proximal portion 702.

As shown in FIG. 7, the proximal portion 702 includes an advancement lumen 706 that is sized and configured to receive the advancement carriage 202 therein and to permit the advancement carriage 202 to move distally therethrough. The advancement plunger 208 is not illustrated in FIG. 7 so that the deployment plunger 228 and associated features thereof may be illustrated more clearly.

The distal portion 704 may include a carriage section 710 that forms another portion of the deployment chamber 213. The deployment carriage 222 is shown within the carriage section 710 in the proximal position 225. A top surface of the carriage body 410 is illustrated along with a top surface 413 of the boss 414. As shown in FIG. 7, the deployment plunger 228 extends from the carriage body 410 through the carriage section 710 and interstitial section 714 and into the folding section 214 (shown in FIG. 2, for example). As discussed above, damping features, such as protruding features 416, may be utilized to maintain a relatively consistent velocity of the deployment carriage 202 as the deployment carriage 202, including the carriage body 410 and the deployment plunger 228, move distally. As also described above, the protruding features 416 may make contact with an inner surface of the deployment chamber 213 or other feature protruding therein in order to provide a damping force that provide resistance to the distal movement of the deployment carriage 222. Damping features may be included in various implementations of the proximal section 104. FIG. 7 includes a dashed line surrounding a portion of the distal section 102 that is shown in greater detail in FIG. 8A.

Figure 8B:
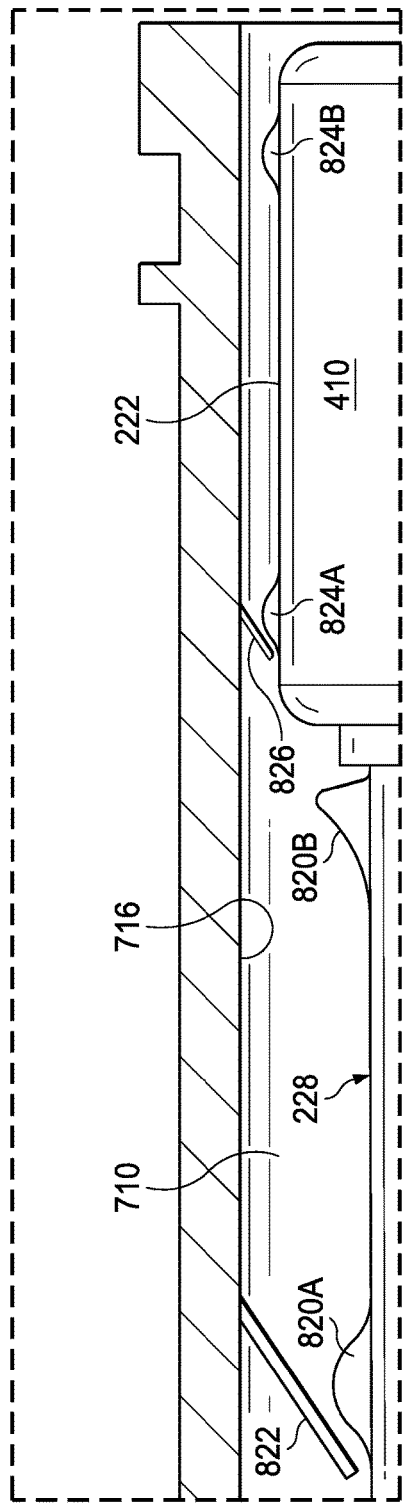

FIGS. 8A, 8B, 8C, 8D, 8E, 8F, and 8G illustrate additional implementations of damping features and damping feature systems according to some exemplary aspects of the present disclosure. As shown in FIG. 8A, a damping feature 802 is depicted as positioned in a distal portion of the carriage section 710. The damping feature 802 may be formed by a membrane 804 that is attached to an inner wall 716 of the carriage section 710. The membrane 804 may be a flexible membrane. For example, in some instances, the membrane 804 may be formed from silicone or other flexible material.

Further, the membrane 804 may define an inner space 806. In some implementations, the damping feature 802 may be formed from a solid material, such that no space 806 is defined therein. Implementations of the damping feature 802 may be either flexible or rigid. FIG. 8A also shows a damping feature 808 that protrudes from a surface of the deployment plunger 228. As illustrated, the damping feature 808 may be an annular feature that is rotationally symmetric about an axis of the deployment plunger 228. In other embodiments, the damping feature 802 may include one or more discrete protrusions extending from the surface of the deployment plunger 228 toward the inner wall 716 of the carriage section 710.

In the illustrated example, as the deployment carriage 222 moves between the initial proximal position 225 and the final distal position 601 within the carriage section 710, the damping features 802 and 808 come into contact providing resistance to movement of the carriage 222 in the distal direction. The positions of the damping features 802 and 808 along the axis A3 may be selected based upon a force profile of the deployment carriage 222 and by resistive forces resulting from contact with the IOL 212 and the interior walls of the distal section 216 that are transferred into the deployment carriage 222 through the deployment plunger 228. For example, a lower amount of force may be required to advance the deployment carriage 222 before the tip 230 of the deployment plunger 228 engages the IOL 212. Additionally, the tip 230 engages the walls of the distal section 216, thereby increasing resistance to movement in the distal direction. As the IOL 212 and the tip 230 are forced within the narrowing region of the distal section 216, a force requirement to maintain a desired rate of movement through the distal section 216 may increase. For example, if a desired constant rate of movement were desired, the force required to maintain that constant rate of movement may increase once the IOL 212 and tip 230 are forced through the narrowing region of the distal section 216. After the IOL 212 passes out of the distal section 216, the force required to continue advancing the deployment carriage 222 may decrease. This force may decrease even further once the tip 230 passes out of the distal section 216. In order to modulate the force applied by the deployment carriage 222, damping features such as the damping features 802 and 808 may be incorporated into various components included within the distal section 102 of the IOL insertion apparatus 100.

When the damping feature 808 contacts the damping feature 802, the features 802 and 808 interact to provide a resistive force that causes movement of the deployment carriage 222 and the deployment plunger 228 in the distal direction to be slower than would otherwise be the case. By positioning damping features where the motion of the deployment plunger 228 and the carriage 222 would be at the highest velocity, the velocity along the full range of movement may be damped to become more consistent. This may permit the IOL 212 to be positioned more accurately and more carefully within a patient's eye. Damping features may be positioned elsewhere within the distal portion 704 of the proximal section 104 of the IOL insertion apparatus 100. For example, a damping feature 810 may be positioned in a distal region of the interstitial section 714. The damping feature 810 may contact the deployment plunger 228 to provide additional resistance to the advancement of the deployment carriage 222. The point at which and the degree to which the damping feature 810 engages the deployment plunger 228 may be varied by an amount of taper of sidewalls 812 of a distal portion 227 of the deployment plunger 228 as well as the size and shape of the damping feature 810.

Other damping features are illustrated in FIGS. 8B-8G. FIGS. 8B-8G depict additional implementations of damping means or systems that may be employed to maintain a desired rate of movement of the deployment carriage 222 and deployment plunger 228 during deployment of the IOL 212 by applying resistance at selected locations. The resistance may be applied at certain positions and at selected magnitudes in order to provide a desired relatively constant rate of movement. As seen in FIG. 8B, a pair of damping features 820A and 820B protrude from the deployment plunger 228. As illustrated, the damping features 820A and 820B have different shapes. In other implementations, the shapes of the damping features 820A and 820B may have the same shape. The damping features 820A and 820B engage a damping feature 822 that protrudes inwardly from the inner wall 716. The damping feature 822 may be a flexible flap that yields resistively to the movement of the damping features 820A and 820B during deployment.

During the first stage of the deployment of the IOL 212, the damping feature 822 and the damping feature 820A contact each other to provide added resistance to movement of the deployment carriage 222 and deployment plunger 228 in the distal direction. During a second stage of the deployment of the IOL 212, the damping feature 822 may not contact any portion of the deployment plunger 228, such that the damping feature 822 does not provide added resistance to the movement of the deployment carriage 222 and deployment plunger 228 in the distal direction. During a third stage, the damping feature 822 may contact the proximally positioned damping feature 820B. The interaction between the damping features 822 and 820B provides added resistance to the movement of the deployment carriage 222 and deployment plunger 228 in the distal direction towards the end of the movement. For example, the interaction between the damping features 822 and 820B may provide added resistance after the compressible tip 230 passes outside of the distal section 216 of the deployment chamber 213.

Also as shown in FIG. 8B, a pair of protruding damping features 824A and 824B may extend from the carriage body 410 toward the inner wall 716. A damping feature 826, shown as a flap, may protrude inwardly from the inner wall 716 and contact the damping features 824A and 824B to increase resistance to the movement of the deployment carriage 222 at initial and final stages of such movement.

Figure 8C:
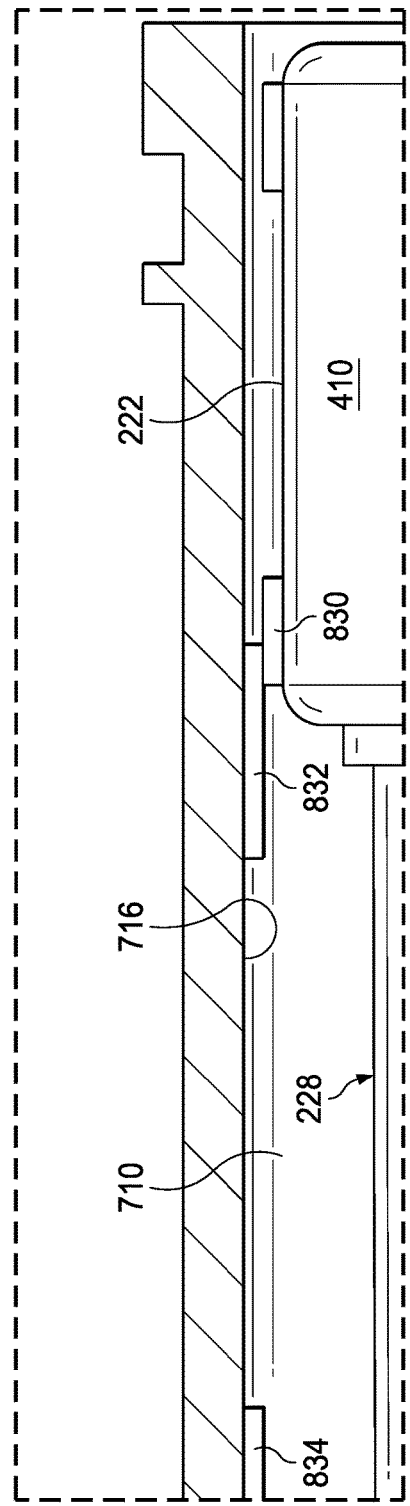

FIG. 8C shows another exemplary implementation of a damping system that functions to control the distal movement of the deployment carriage 222. As shown in FIG. 8C, a damping feature 830 protrudes from the carriage body 410 toward the inner wall 716. In an initial position, the damping feature 830 may be disposed in contact with a damping feature 832 formed on the inner wall 716 and protruding inwardly therefrom. The damping features 830 and 832 may be frictional pads that generate resistive force when the damping features 830 and 832 engage one another. As the deployment carriage 222 moves distally, the damping feature 830 may cease contacting the damping feature 832 and may enter into contact with another damping feature 834. As shown, the damping features 830, 832, and 834 may be substantially planar. However, other implementations of the damping features of FIG. 8C may have tapered profiles, undulating profiles, or otherwise regular or irregular profiles, that modulate a resistive force applied to the carriage 222 to provide a more constant rate of movement the deployment carriage 222 during deployment of the IOL 212. The damping features 832, 832, and 834 (as well as other damping features described herein) may have a textured surface to increase friction.

Referring now to FIG. 8D, shown therein are additional implementations of damping features according to the present disclosure. A solid damping feature 830 protrudes inwardly from the inner wall 716. In some implementations, the damping feature 830 may be formed from silicone and affixed to the inner wall 716. In other implementations, the damping feature 830 may be formed from the same material as the proximal section 104 of the IOL insertion apparatus 100, which may be formed from a polymeric material or other suitably rigid material. Thus, in some implementations, the damping feature 830 may form an integral part of the inner wall 716 that projects inwardly into the carriage section 710. The damping feature 830 is positioned to contact the damping feature 832 during the movement of the deployment carriage 222. Additionally, a flexible damping feature 834 may protrude inwardly from the inner wall 716 near the deployment carriage 222 when the deployment carriage 222 is located at the proximal position 225, as shown in FIG. 8D.

FIG. 8E shows a damping feature 840 that includes a flywheel 842 that is maintained in contact with the inner wall 716 by a spring member 844 that pushes the flywheel 842 radially outwardly from the deployment plunger 228. In some implementations, the flywheel 842 may have one or more gears to increase resistance to the rotation thereof. In this way, the flywheel 842 may provide resistance to the distal movement of the deployment carriage 222 during deployment of the IOL 212. In some implementations, the spring member 844 may be limited such that the flywheel 842 does not contact the inner wall 716 but may, instead, contact damping features extending inwardly from the inner wall 716. In this way, the flywheel 842 may provide resistance only at specific portions of the distal movement of the deployment carriage 222.

Figure 8F:
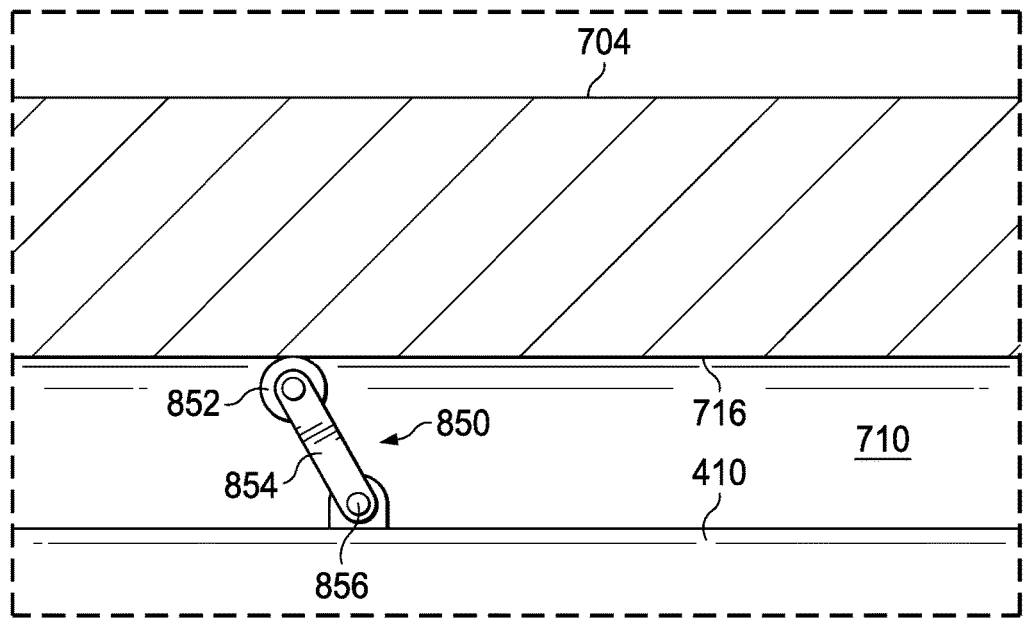
Figure 8G:
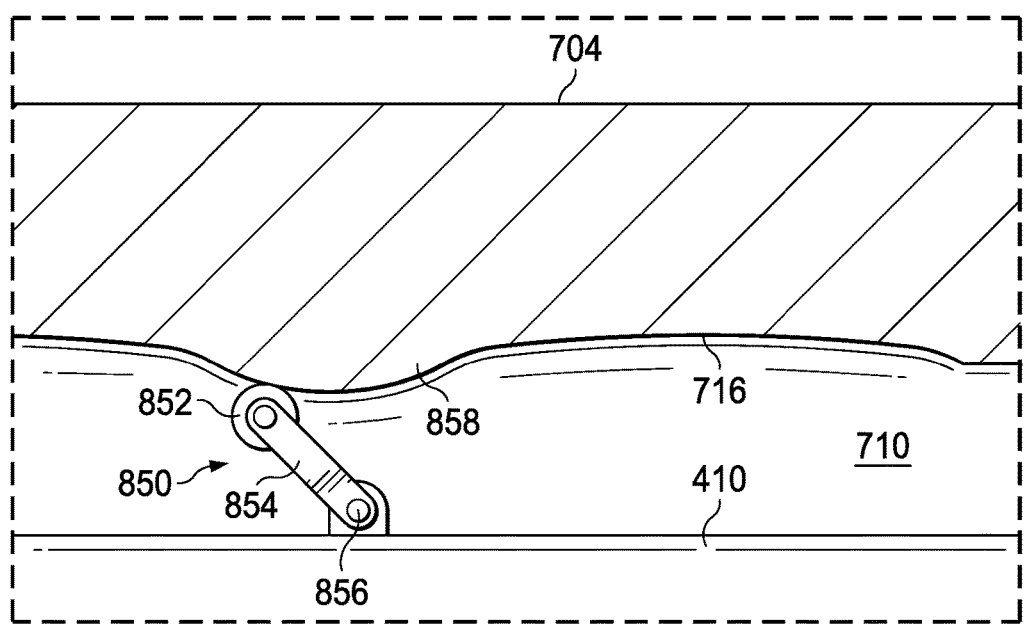

Referring now to FIGS. 8F and 8G, shown therein are additional implementations that include a wheel to provide selective resistance to distally directed motion of the deployment carriage 222. As shown in FIGS. 8F and 8G, a damping feature 850 extends between the carriage body 410 and the inner wall 716 of the carriage section 710. The damping feature 850 may include a wheel 852 disposed at a distal end of a beam 854. The beam 854 may be coupled at a proximal end to the carriage body 410 by a hinge 856. The hinge 856 may permit an angle formed between the beam 854 and the carriage body 410 to change as the carriage 222 moves, such as in the distal direction. The hinge 856 may contain a spring or another mechanism to bias the damping feature 850 to maintain contact with the inner wall 716 by providing a rotational force at the hinge 856. While the inner wall 716 is illustrated as being substantially flat in FIG. 8F, FIG. 8G shows an implementation in which the inner wall 716 includes topographical features, such as bulge 858. The bulge 858 may be a curved feature formed in the inner wall 716. In some implementations, the bulge 858 may protrude inwardly from the inner wall 716. As the wheel 852 follows the bulge 858, the beam 854 is pivoted about the hinge 856 against a force provided by a biasing element contained therein. Engagement between the damping feature 850 and the surface bulge 858 changes the angle between the inner wall 716 and the carriage body 410 and increases a resistance to movement of the carriage body 410. Alternatively, a concave feature formed in the inner wall 716 would lessen a resistive force generated by the damping feature 850.

Combinations of the damping features of FIGS. 7 and 8A-G are within the scope of this disclosure. For example, some implementations may include frictional pads, like the features 830 and 832, the flap-like feature 822, and a corresponding feature 820A formed on or coupled to the deployment plunger 228. Any suitable combination of damping feature shape and material is contemplated. The damping features may be located in any portion of the deployment chamber 213. Any combinations are included within the scope of this disclosure. The damping features may surround the deployment plunger 228 or the carriage body 410, in some implementations. Other implementations may include pairs of opposing damping features. In some implementations, the damping features present on the carriage body 410 may extend into a recess formed in the inner wall 716. In such implementations, corresponding damping features may extend inwardly from the recess or recesses. For example, the protruding features 416 shown in FIG. 4 may function both to guide the motion of the deployment carriage 222 and to interact with one or more damping features, like the damping feature 826 of FIG. 8B or any other damping feature that protrudes inwardly from or formed in the inner wall.

Figure 9:
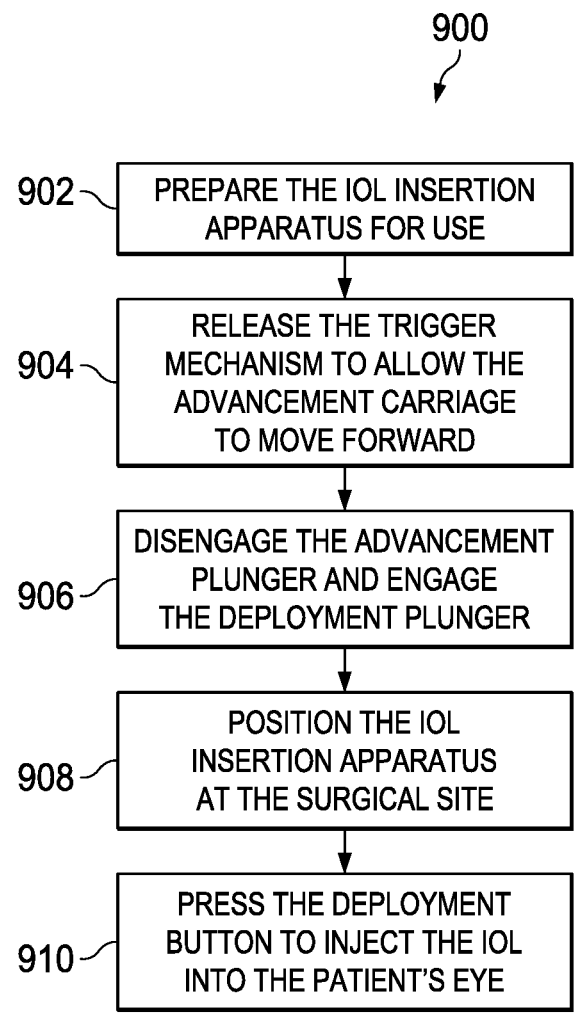
FIG. 9 is a flowchart showing a method for using the IOL insertion apparatus that provides automated advancement and deployment of the IOL.

FIG. 9 is a flowchart showing an illustrative method for using an IOL insertion apparatus that provides automated advancement and deployment of the IOL, such as, for example, the IOL insertion apparatus 100 described herein. According to the present implementation, the method 900 includes a step 902 for preparing the IOL insertion apparatus for use. Preparing the IOL for use may include removing an IOL lockout mechanism that prevents movement of the plungers and the IOL. Step 902 may also include injecting a lubricant into the handpiece body, such as a viscoelastic solution. In some implementations, the IOL insertion apparatus may be pre-packaged with the IOL located proximally outside of the folding chamber in an unfolded state. The IOL may also be secured in place through an IOL lockout mechanism. The IOL lockout mechanism may be a mechanical piece attached to the exterior of the handpiece body, such as the handpiece body 101 shown in FIG. 1. When attached to the handpiece body, the IOL lockout mechanism in the form of a mechanical piece mechanically secures the IOL in place to protect it from unwanted movement during shipping. The IOL lockout mechanism may also mechanically block distal motion of the advancement carriage to avoid premature triggering of the folding process.

After the IOL lockout mechanism has been removed, an operator may inject or otherwise add a lubricant into the handpiece body. The lubricant may fill a space around the IOL in the folding chamber to provide lubrication for the IOL as the IOL passes through the folding chamber. In some implementations, the lubricant may be an Ophthalmic Visiosurgical Device (OVD) fluid.

The method 900 also includes a step 904 for releasing a trigger mechanism to allow the advancement carriage, such as, for example, the advancement carriage 202, to move distally. As described above, the operator may press a button, such as, for example, advancement trigger 106, that mechanically releases the advancement carriage. The advancement carriage may be biased to move in the distal direction. In such instances, the advancement carriage moves from a first, proximal position to a second, distal position within the handpiece body. An advancement plunger, such as, for example, advancement plunger 208, may be coupled to the advancement carriage, and forward motion of the advancement carriage causes forward motion of the advancement plunger. The advancement plunger engages the IOL and moves the IOL out of its original placement and through the folding chamber. Passage of the IOL through the folding chamber causes the IOL to be folded before it is inserted into the patient's eye.

The method 900 also includes a step 906 for disengaging the advancement plunger from the IOL and engaging a deployment plunger, such as, for example, deployment plunger 228 described above, with the IOL. The advancement plunger may be disengaged and the deployment plunger aligned for engagement with the IOL, for example, by pulling, rotating, and pushing a proximal section (e.g., proximal section 104) of the IOL insertion apparatus relative to a distal section (e.g., distal section 102) of the IOL insertion apparatus as described above.

The method 900 further includes a step 908 for positioning the IOL insertion apparatus at the surgical site. In some implementations, a small incision is made in the patient's eye at the surgical site. In some implementations, the incision may be less than 2 millimeters. Placement of the IOL insertion apparatus involves placing a distal tip of the IOL insertion apparatus, e.g., distal tip 112, at the incision such that, when the IOL is moved out of the distal tip, the IOL is passed through the incision and into the eye of the patient.

The method 900 further includes a step 910 for deploying the IOL into the eye. Deployment of the IOL into the eye may be performed by pressing a deployment button to inject the IOL into the patient's eye. As described above, pressing the deployment button releases the deployment plunger and allows a spring system of the deployment carriage to move the deployment plunger forward. Forward motion of the deployment plunger moves the IOL out of the distal tip of the IOL insertion apparatus, through the incision, and into the patient's eye. This forward motion may be influenced by damping features, such as any one or more of the damping features described herein. Resistance may be selectively applied to the forward motion to make a rate of movement of the deployment plunger more consistent along an entire path of movement.

Use of methods and systems described herein provides a number of benefits and advantages. For example, because deployment of the IOL is automated rather than relying on varying human operators, there is less risk that the IOL will be deployed improperly. Furthermore, deployment of the IOL as described herein does not rely on any external power or connection. Instead, automated deployment of the IOL is done mechanically with the use of spring systems described herein. Damping features are provided to make the rate of movement while advancing deploying the IOL more consistent, resulting in a more predictable surgical process.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraocular lens (IOL) insertion apparatus comprising:
a handpiece body comprising a distal tip;
a deployment chamber formed within the handpiece body and defining an opening at a distal end of the handpiece body, a portion of the deployment chamber sized and shaped to hold a folded IOL;
a deployment system disposed within the handpiece body, the deployment system comprising:
a deployment carriage movable between an initial proximal position and a final distal position within the handpiece body; and
a deployment plunger comprising a shaft having a proximal end secured to the deployment carriage and having a distal end adapted to engage a folded IOL;
a first damping feature protruding from one of a wall of the deployment chamber and a portion of the deployment system, the first damping feature being positioned and arranged to increase resistance to movement of the deployment system along a portion of movement between the initial proximal position and the final distal position; and
a second damping feature extending outwardly from the other of the wall of the deployment chamber and a portion of the deployment system, wherein the first damping feature is disposed to make contact with the second damping feature as the deployment system moves,
wherein the second damping feature extends outwardly from the deployment carriage of the deployment system, and
wherein the second damping feature comprises a wheel that contacts the wall of the deployment chamber.

2. The apparatus of claim 1, wherein the second damping feature extends outwardly from the shaft of the deployment plunger.

3. The apparatus of claim 1, wherein the first damping feature comprises at least one flexible spring structure.

4. The apparatus of claim 1, wherein the first damping feature is structurally arranged to provide a frictional engagement between the deployment chamber and the deployment system at a plurality of different positions between the initial proximal position and the final distal position.

5. The apparatus of claim 4, wherein the first damping feature is textured to provide the frictional engagement.

6. The apparatus of claim 1, further comprising a third damping feature protruding inwardly from the wall of the deployment chamber.

7. The apparatus of claim 1, wherein the first damping feature is disposed to contact a body of the deployment carriage as the deployment carriage moves towards the final distal position.

8. An intraocular lens (IOL) insertion apparatus comprising:
a handpiece body comprising a distal tip;
a deployment chamber formed within the handpiece body and forming an opening located at a distal end of the handpiece body;
a lens deployment system disposed within the handpiece body, the deployment system comprising:
a deployment carriage movable between a first position and a second position within the handpiece body; and
a deployment plunger comprising a shaft having a proximal end secured to the deployment carriage and a distal end adapted to engage a lens during deployment thereof; and
a first damping feature protruding outwardly from the lens deployment system that increases frictional resistance to movement of the deployment system during a portion of movement between an initial proximal position and a final distal position, wherein the first damping feature comprises:
- a contact wheel that contacts a portion of the deployment chamber; and
- a hinged beam coupling the contact wheel to the lens deployment system, the hinged beam comprising a hinge that is bendable to maintain contact between the contact wheel and an inner wall of the portion of the deployment chamber.

9. The apparatus of claim 8, wherein the deployment carriage comprises a spring system that biases the deployment carriage in a distal direction towards the final distal position.

10. The apparatus of claim 8, wherein the wheel includes one or more gears that provide resistance to the movement.

11. The apparatus of claim 8, further comprising a second damping feature protruding from an inner wall of a portion of the deployment chamber, wherein the first damping feature and the second damping feature contact each other during at least a portion of the movement of the deployment carriage to provide resistance to the movement of the deployment carriage.

12. The apparatus of claim 11, further comprising a third damping feature protruding from the inner wall of the portion of the deployment chamber, the third damping feature offset from the second damping feature along a central axis of the deployment chamber.

13. The apparatus of claim 11, wherein the first damping feature is rigid and wherein the second damping feature comprises a flexible membrane.

14. An intraocular lens (IOL) insertion apparatus comprising:
a handpiece body comprising:
- a proximal section; and
- a distal section, the distal section being rotatable relative to the proximal section between a first rotational position and a second rotational position, the second rotational position aligning a deployment plunger with an IOL deployment chamber;

a deployment carriage connected to a proximal end of the deployment plunger and releasably secured within the handpiece body by a deployment button, the deployment carriage comprising a first set of springs to bias the deployment carriage to move in a distal direction; and a first damping feature protruding inwardly from a wall of the IOL deployment chamber, wherein the first damping feature makes contact with the deployment carriage or the deployment plunger during a portion of movement of the deployment carriage as the deployment carriage moves in the distal direction to provide resistance to the movement of the deployment carriage.

15. The apparatus of claim 14, further comprising:
an advancement plunger; and
an advancement carriage connected to a proximal end of the advancement plunger and releasably secured within the handpiece body by a trigger mechanism, the advancement carriage comprising a second set of springs to bias the advancement carriage to move in the distal direction.

16. The apparatus of claim 14, further comprising a second damping feature protruding outwardly from the deployment carriage, the second damping feature disposed proximally from the first damping feature and positioned to contact the first damping feature when the deployment carriage moves from an initial proximal position to a final distal position.

\* \* \* \* \*